(12) United States Patent
Arcand

(10) Patent No.: US 8,685,011 B2
(45) Date of Patent: *Apr. 1, 2014

(54) TUNICA ABLATION

(75) Inventor: Benjamin Arcand, Minneapolis, MN (US)

(73) Assignee: AMS Research Corporation, Minnetonka, MN (US)

( * ) Notice: Subject to any disclaimer, the term of this patent is extended or adjusted under 35 U.S.C. 154(b) by 18 days.

This patent is subject to a terminal disclaimer.

(21) Appl. No.: 13/327,012

(22) Filed: Dec. 15, 2011

(65) Prior Publication Data

US 2012/0157978 A1 Jun. 21, 2012

Related U.S. Application Data

(60) Provisional application No. 61/423,478, filed on Dec. 15, 2010.

(51) Int. Cl.
*A61B 18/22* (2006.01)

(52) U.S. Cl.
USPC .................................. 606/15; 606/11; 606/41

(58) Field of Classification Search
USPC ............................................... 606/11, 41, 15
See application file for complete search history.

(56) References Cited

U.S. PATENT DOCUMENTS

| | | | |
|---|---|---|---|
| 5,428,699 A | 6/1995 | Pon | |
| 5,651,786 A * | 7/1997 | Abela et al. | 606/15 |
| 6,554,824 B2 | 4/2003 | Davenport et al. | |
| 6,986,764 B2 | 1/2006 | Davenport et al. | |
| 7,447,409 B2 | 11/2008 | Griffin | |
| 2005/0288665 A1* | 12/2005 | Woloszko | 606/41 |
| 2006/0189967 A1* | 8/2006 | Masotti et al. | 606/15 |
| 2007/0185474 A1 | 8/2007 | Nahen | |
| 2009/0105698 A1 | 4/2009 | Hodel et al. | |
| 2009/0131931 A1* | 5/2009 | Lee et al. | 606/41 |
| 2010/0061412 A1 | 3/2010 | Reed, Jr. et al. | |
| 2010/0135617 A1 | 6/2010 | Novak, Jr. et al. | |
| 2011/0288392 A1* | 11/2011 | de la Rama et al. | 600/374 |
| 2013/0237975 A1 | 9/2013 | Arcand | |

* cited by examiner

*Primary Examiner* — Bill Thomson
*Assistant Examiner* — Jeffrey Lipitz
(74) *Attorney, Agent, or Firm* — Brian D. Kaul; Westman, Champlin & Koehler, P.A.

(57) ABSTRACT

In a method of ablating a tunica of a patient, a laser fiber is inserted into the tunica of the patient. Portions of the tunica are exposed to laser light discharged from the laser fiber. The portions of the tunica that are exposed to the laser light are ablated. In one embodiment, a device is used to control the exposure of the tunica to the laser light. In one embodiment, a penile prosthesis is implanted in the ablated tunica.

12 Claims, 5 Drawing Sheets

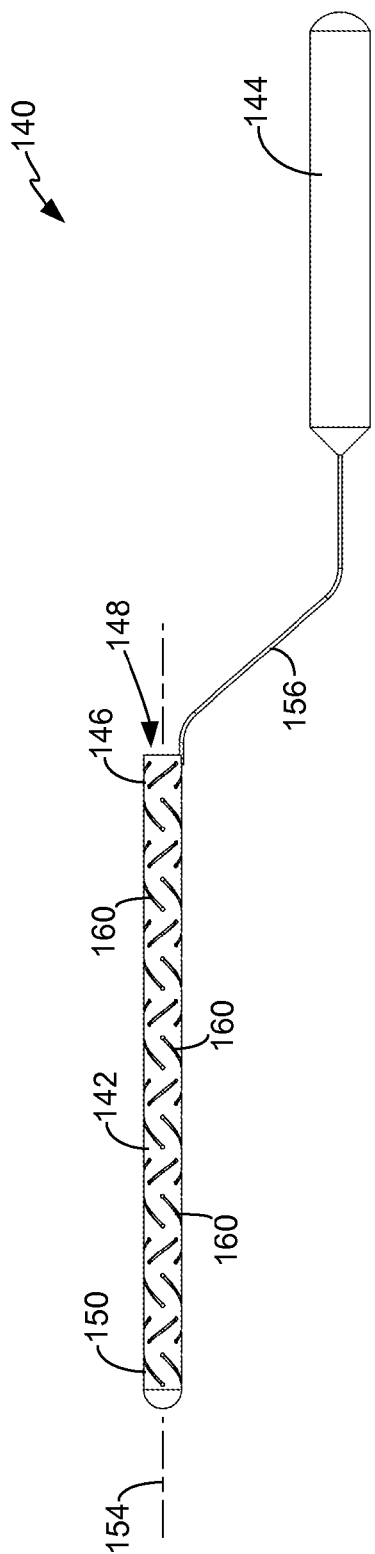
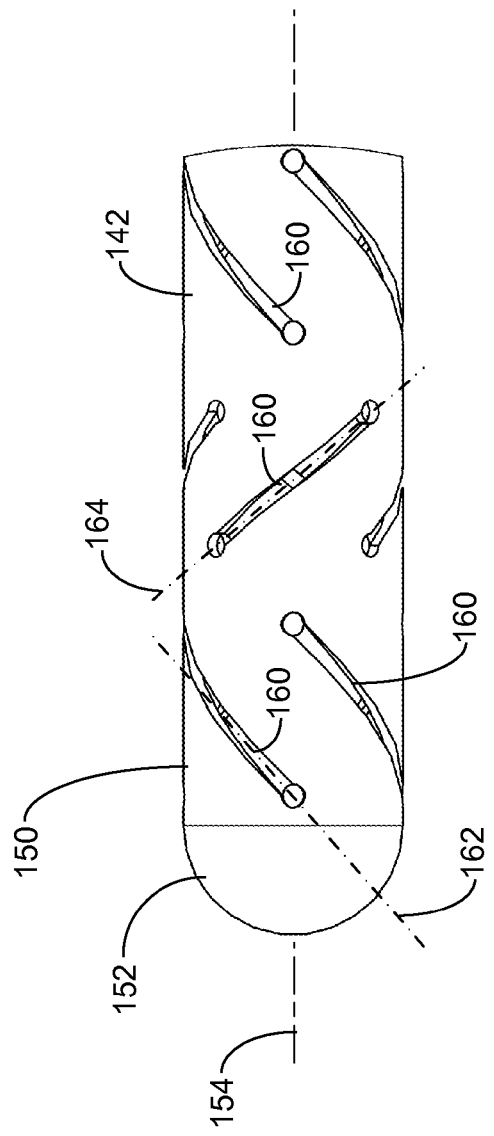

TUNICA ABLATION

CROSS-REFERENCE TO RELATED APPLICATION

The present application is based on and claims the benefit of U.S. provisional patent application Ser. No. 61/423,478, filed Dec. 15, 2010, the content of which is hereby incorporated by reference in its entirety.

FIELD

Embodiments of the invention are directed to methods of treating a condition of the penis that include the selective ablation of portions of the tunica, and devices for use in the methods.

BACKGROUND

There are various types of penile prostheses that may be implanted in the corpus cavernosa of the penis to treat erectile dysfunction. Two common types of penile prostheses are non-inflatable, semi-rigid and malleable prostheses, and inflatable prostheses.

The corpus cavernosa is surrounded by a sheath known as the tunica albuginea (hereinafter "tunica"). The tunica is a fairly non-compliant membrane that limits the expansion of the corpus cavernosa. Thus, the tunica limits the size of the semi-rigid penile prosthesis that can be implanted in the corpus cavernosa as well as the amount an inflatable penile prostheses can be expanded within the corpus cavernosa. As a result, the overall size of the erect penis is limited by the tunica.

Peyronie's disease is a disfiguring condition of the penis caused by scarring of the tunica. The scarred tunica causes curvature of the erect penis.

SUMMARY

Embodiments of the invention are directed to methods of treating a condition of the penis that include the selective ablation of portions of the tunica. The methods may be used to treat erectile dysfunction and Peyronie's disease, for example.

In one embodiment, a laser fiber is inserted into the tunica of a patient. Portions of the tunica are exposed to laser light discharged from the laser fiber. The portions of the tunica that are exposed to the laser light are ablated. In accordance with one embodiment of the method, a penile prosthesis is implanted in the ablated tunica.

Another embodiment is directed to a device that may be used in the method. One embodiment of the device comprises a cylindrical tube having an open proximal end and a plurality of openings in a wall of the tube. In one embodiment, the device includes a handle that is attached to the proximal end of the cylindrical tube. The device may be used in the method described above to control the exposure of the tunica to the laser light discharged from the laser fiber.

Other features and benefits that characterize embodiments of the present disclosure will be apparent upon reading the following detailed description and review of the associated drawings.

BRIEF DESCRIPTION OF THE DRAWINGS

FIG. 6 is a side view of a device in accordance with embodiments of the invention.

FIG. 7 is a magnified view of the distal end of the device of FIG. 6.

DETAILED DESCRIPTION OF ILLUSTRATIVE EMBODIMENTS

Embodiments of the invention are directed to methods of treating a condition of the penis that include the selective ablation of portions of the tunica. Embodiments of the methods include the treatment of erectile dysfunction and Peyronie's disease, for example. Another embodiment is directed to a device that can be used to assist in the selective ablation of the tunica.

Figure 1:
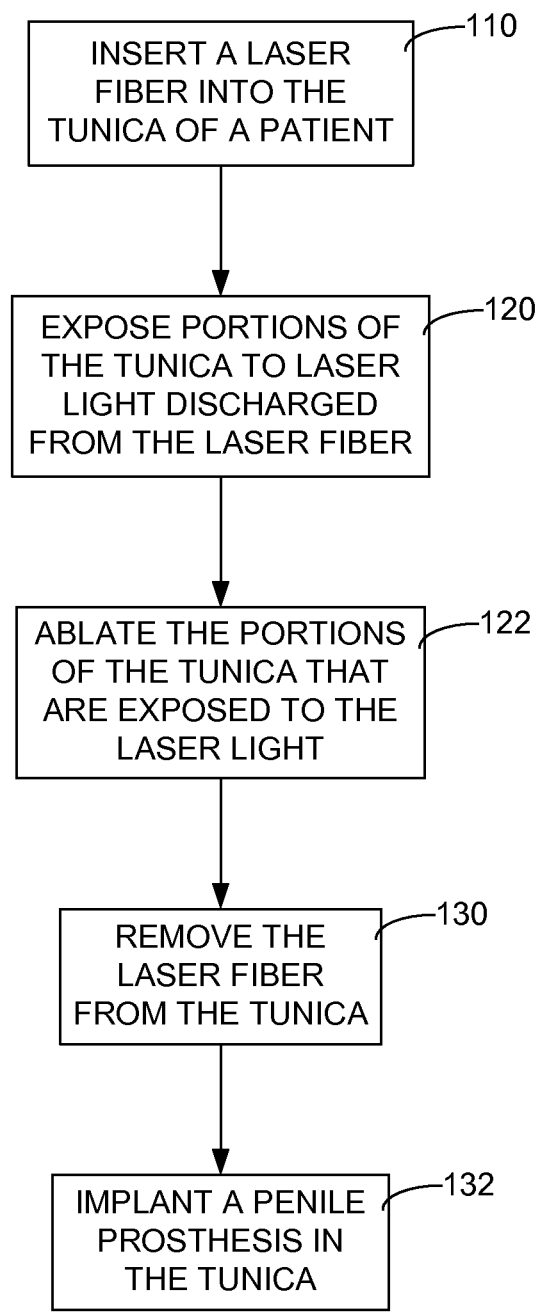
FIG. 1 is a flowchart illustrating a method in accordance with embodiments of the invention.

FIG. 1 is a flowchart illustrating methods of ablating the tunica of a patient and treating erectile dysfunction of the patient, in accordance with embodiments of the invention. Steps of the method will be described with reference to FIGS. 2-5.

Figure 2:
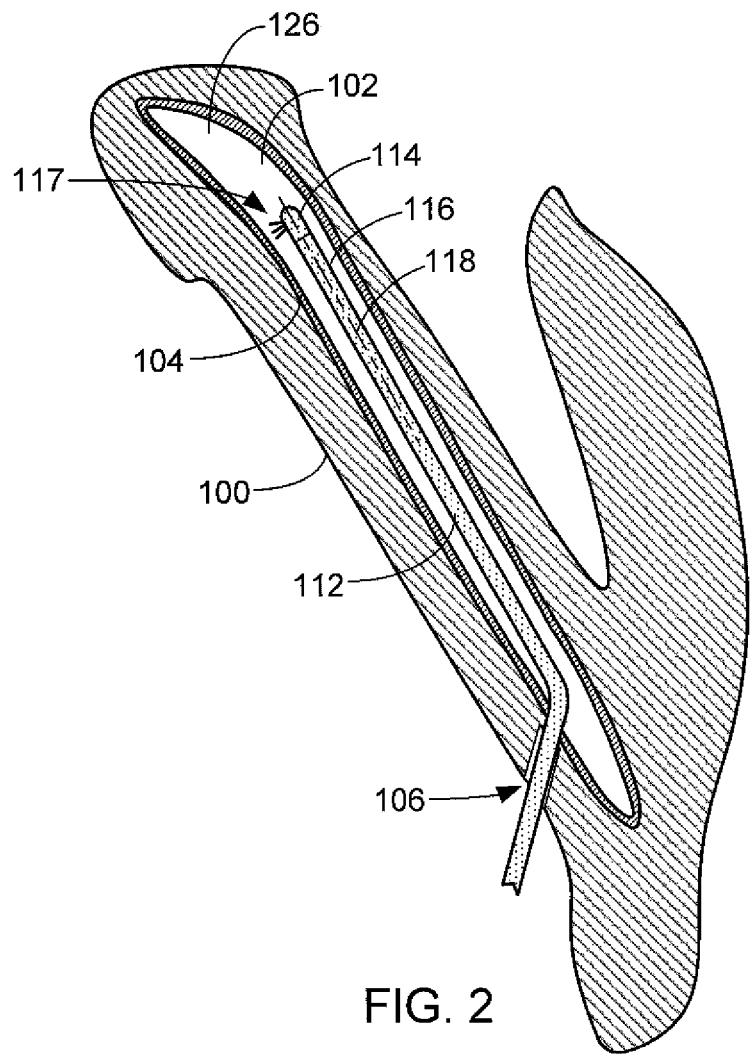
FIG. 2 is a simplified cross-sectional view of a penis illustrating steps of the method.

FIG. 2 is a simplified side cross-sectional view of a penis 100 illustrating method steps in accordance with embodiments of the invention. Some of the anatomical features illustrated in FIG. 2 include the corpus cavernosa 102 and the tunica 104, which surrounds the corpus cavernosa 102.

In one embodiment, the patient is initially prepped for implantation of a penile prosthesis by making an incision 106 at the base of the penis and dilating the corpus cavernosa 102 in accordance with conventional techniques.

At step 110 of the method, a laser fiber 112 is inserted within the tunica 104 of the patient, such as through the incision 106, as shown in FIG. 2. Embodiments of the laser fiber 112 comprise an optical fiber or other waveguide that is configured to deliver electromagnetic energy in the form of laser light to a probe tip 114 located at a distal end 116 of the laser fiber 112. The probe tip 114 is configured to discharge the laser light 117 in a desired direction or pattern, such as in a radial direction relative to a central axis 118 of the laser fiber 112, as shown in FIG. 2. The probe tip 114 may also be configured to discharge laser light in a 360 degree pattern about the central axis 118. Other conventional probe tips 114 may be used to provide a desired pattern of the discharged laser light 117.

In one embodiment, the laser fiber 112 is coupled to a laser system configured to generate the laser light 117. Embodiments of the laser system include conventional laser systems for producing laser light 117 for use in laser ablation treatments. In one embodiment, the laser system produces laser light 117 in the form of a frequency double Nd:YAG laser, which operates at 532 nm, which has been used to effectively ablate tissue.

At step 120 of the method, portions of the tunica 104 are exposed to the laser light 117 discharged from the laser fiber 112. At step 122, the portions of the tunica 104 that are exposed to the laser light 117 in step 120 are ablated to deliberately weaken the portions of the tunica 104. At step 130, the laser fiber 112 is removed from the tunica 104 through the incision 106. This process may then be repeated on the other tunica of the patient.

In one embodiment of step 120, the laser light 117 is discharged in pulses from the laser fiber 112 as the laser fiber 112 moves relative to the tunica 104. In one embodiment, the pulsing of the discharged laser light 117 may be controlled by the operator or through settings of the laser system.

Figure 3:
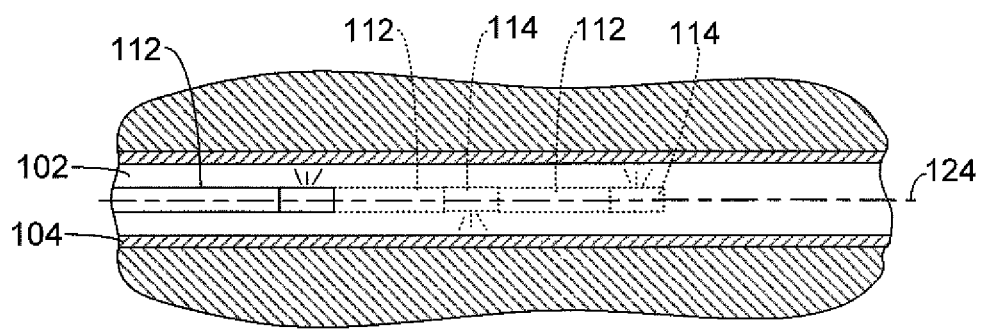
FIGS. 3 and 4 are cross-sectional views of the tunica of a patient illustrating tissue ablating steps in accordance with embodiments of the method.

In one embodiment of step 120, the pulses of the laser light 117 are discharged from the laser fiber 112 within the tunica 104 as the laser fiber is moved relative to the tunica 104 along a longitudinal axis 124 of the tunica 104, as illustrated schematically in the side cross-sectional view of a portion of the tunica provided in FIG. 3. In one embodiment, the pulses of laser light 117 are discharged from the probe tip 114 of the laser fiber 112 as the laser fiber 112 is fed into the tunica 104. In accordance with another embodiment, the distal end 116 of the laser fiber 114 is fed to the distal end 126 of the tunica and the pulses of the laser light 117 are discharged from the probe tip 114 as the laser fiber is drawn out of the tunica 104.

Figure 4:
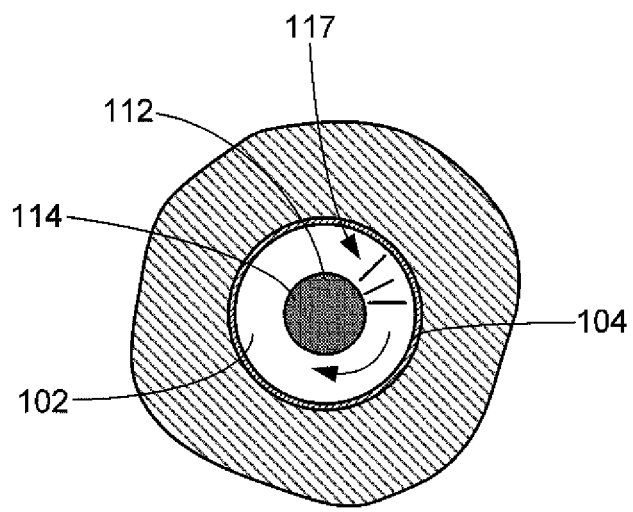

In one embodiment, the laser fiber 112 is rotated about the central axis 118 during the discharge of the laser light 117 from the probe tip 114 during the method step 120, as illustrated in the simplified cross-sectional view provided in FIG. 4. In one embodiment, pulses of the laser light 117 are discharged from the probe tip 114 of the laser fiber 112 as the laser fiber 112 is both moved along the axis 124 and rotated about the axis 118 within the tunica 104.

In one embodiment of the ablating step 122, the ablated portions of the tunica 104 are displaced from each other such that the ablated portions are surrounded by non-ablated portions. In one embodiment, this results in a pattern of ablated portions in the tunica 104. The ablated portions form weak points in the tunica 104 that form openings in the tunica 104 after the tunica 104 has been allowed to heal. In one embodiment, the openings in the tunica allow the tunica 104 to dilate and lengthen more than would be possible without the openings.

In one embodiment, the ablated portions of the tunica 104 allow the tunica 104 to expand along the longitudinal axis 124. In one embodiment, the ablated portions of the tunica 104 allow the tunica 104 to expand radially from the longitudinal axis 124. In one embodiment, the ablated portions of the tunica 104 allow the tunica 104 to expand both along the longitudinal axis 124 and radially from the longitudinal axis 124.

As mentioned above, one embodiment of the method involves treating erectile dysfunction of the patient. In accordance with this embodiment, a penile prosthesis 134 is implanted in the ablated tunica 104 in accordance with conventional techniques, as illustrated schematically in the cross-sectional view of the tunica provided in FIG. 5. The ablation and implantation steps may also be performed on the other tunica of the patient to complete the restoration. Embodiments of the penile prosthesis 134 include conventional prostheses including inflatable and non-inflatable prostheses.

One advantage to the increased expandability of the tunica 104 is that the tunica 104 can accommodate penile prostheses 134 having a larger length and diameter than would be possible if conventional penile erectile reconstruction techniques were used. This allows the treatment to also enlarge the size of the erect penis 100. In one embodiment, the penile prosthesis 134 is in the form of an inflatable prosthesis and is expanded gradually during the healing process to allow healing of the tunica 104 to occur in a dilated and lengthened state.

One embodiment of the invention is directed to a device that may be used in the above described method. FIG. 6 is a side view of an exemplary device 140 in accordance with embodiments of the invention. In one embodiment, the device 140 comprises a cylindrical tube 142 and a handle 144 attached to the tube at a proximal end 146. The tube 142 has an opening 148 at the proximal end 146. In one embodiment, the device 140 includes a closed distal end 150. In one embodiment, the distal end 150 includes a blunt end cap 152, as shown in the partial side view of the distal end 150 of the tube 142 provided in FIG. 7.

In one embodiment, the tube 142 has a central axis 154 and the handle 144 is displaced from the central axis 154, as shown in FIG. 6. In one embodiment, the handle 144 is attached to the proximal end 146 of the tube 142 through a bent rod 156. In one embodiment, the handle 144 is aligned substantially parallel to the central axis 154 of the tube 142.

Figure 8:
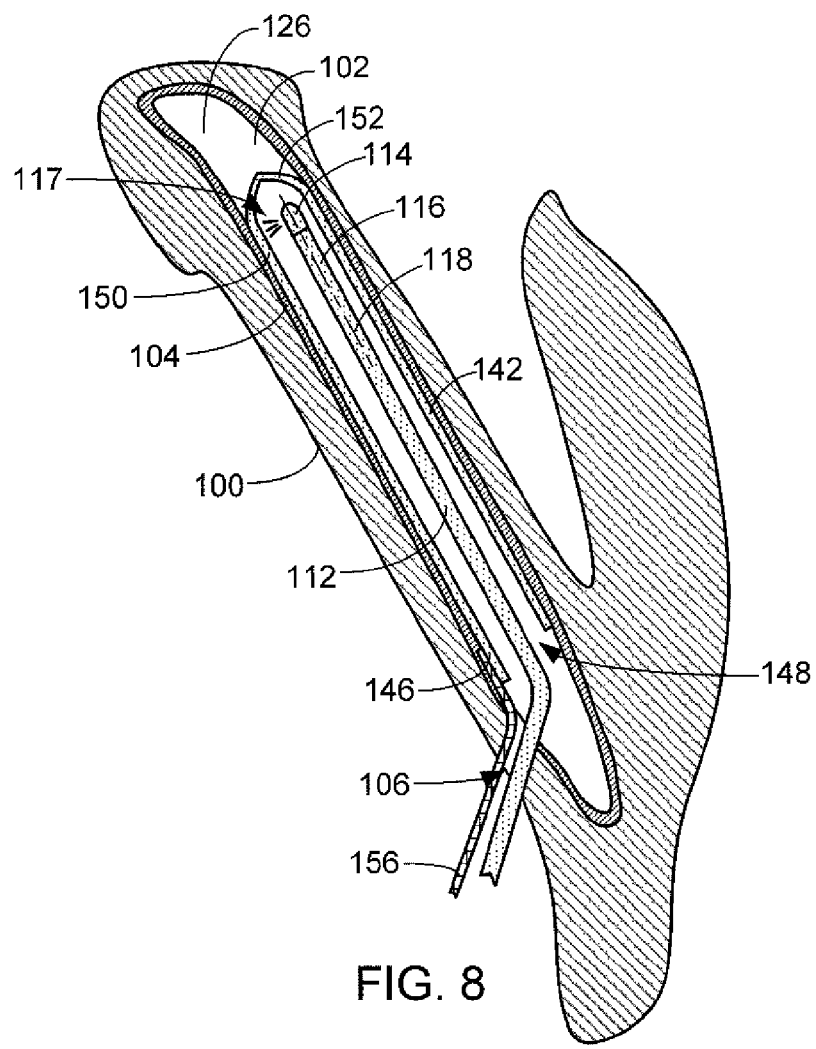
FIG. 8 is a simplified side cross-sectional view of a penis illustrating steps of the method in accordance with embodiments of the invention.

In one embodiment, the tube 142 is configured to be inserted into the corpus cavernosa 102 and the tunica 104, as shown in FIG. 8, to assist in the method described above. In one embodiment, the tube 142 is inserted through the incision 106 prior to performing the laser fiber insertion step 110 of the method. In one embodiment, the insertion of the tube 142 in the corpus cavernosa 102 and the tunica 104 dilates the tunica 104. In one embodiment, the tube 142 has an outer diameter of approximately 5-15 millimeters.

In one embodiment, the method step 110 is performed by inserting the distal end 116 of the laser fiber through the opening 148 of the tube 142. The distal end 116 of the laser fiber 112 is then positioned within the tube 142 as desired, such as toward the distal end 126 of the tunica 104, as shown in FIG. 8.

In one embodiment, the tube 142 is formed of glass or other material that is transparent to the laser light 117. In accordance with this embodiment, the method step 120 is performed in accordance with the embodiments described above where the laser light 117 is pulsed to generate the desired ablation pattern in the tunica 104. Here, the tube 142 operates primarily to dilate the tunica 104 and provide a path for the laser fiber 112.

In accordance with another embodiment, the device 140 operates as a mask for the ablation process by allowing only a portion of the discharged laser light 117 to reach the tunica 104 in the exposing step 120. In this embodiment, the tube 142 is formed of a material that blocks the laser light 117, such as stainless steel or other suitable material.

In one embodiment, the tube 142 includes a plurality of openings 160 through the wall of the tube 142, as shown in FIG. 7. The openings 160 are located in a desired pattern about the tube 142. The openings 160 in the tube 142 define the locations where the laser light 117 can pass to expose the portions of the tunica 104 located at the openings 160. Thus, the pattern of the openings 160 define the locations where the tunica 104 can be exposed to the laser light 117. Accordingly, the pattern of openings 160 determines the ablation pattern of the tunica in step 122.

In one embodiment, the openings 160 are in the form of slits as shown in FIG. 7. The slit shaped openings 160 cause a corresponding ablation pattern to form on the tunica 104. The ablated portions of the tunica 104 correspond to the slit shaped openings 160 and allow the tunica 104 to stretch and increase the overall surface area of the tunica and the size of the penis. In one embodiment, the longitudinal axes of a plurality of the slits 160 are approximately aligned with a first plane 162, as shown in FIG. 7. In one embodiment, the longitudinal axes of a plurality of the slits 160 are approximately aligned with a second plane 164. In one embodiment, the slits 160 have a length of 1-15 mm. In one embodiment, the slits 160 have a width of 0.1-5.0 mm.

In one embodiment of the exposing step 120, the laser fiber 112 is moved relative to the tunica 104 and the tube 142 as the laser light 117 is discharged from the probe tip 114. A portion of the laser light 117 is blocked by the wall of the tube 142, and a portion of the laser light 117 is allowed to pass through the openings 160 in the tube 142 and expose the adjacent portions of the tunica 104. Depending on the configuration of the probe tip 114, it may be necessary to rotate the laser fiber 112 about the central axis 118 of the laser fiber 112 as the laser fiber 112 is moved along the longitudinal axis 124 of the tunica 104. For instance, when the probe tip 114 is a side-fire probe tip configured to discharge the laser light 117 laterally relative to the central axis 118 of the laser fiber 112, it may be necessary to rotate the laser fiber 112 about the central axis 118 in order to expose the entire pattern of openings 160 and the corresponding portions of the tunica 104 at a given location along the longitudinal axis 124 of the tunica 104. Alternatively, the probe tip 114 may be configured to discharge the laser light 117 radially over 360 degrees around the central axis 118. For this configuration, it is only necessary to move the laser fiber 112 along the longitudinal axis 124 of the tunica 104 to fully expose the pattern of openings 160 and the exposed portions of the tunica 104.

Figure 9:
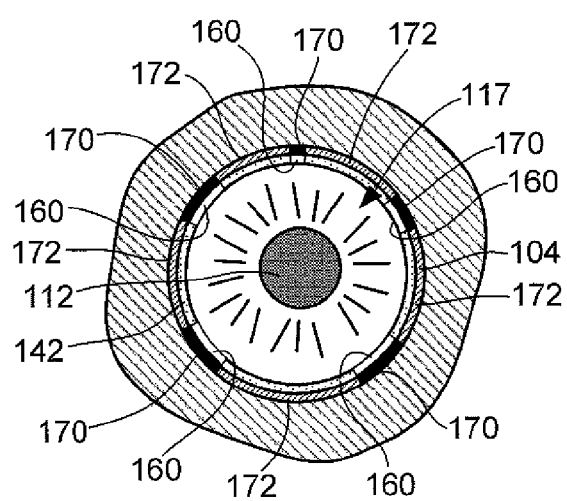
FIG. 9 is a cross-sectional view of the tunica illustrating an exemplary ablating step in accordance with embodiments of the method.

FIG. 9 is a cross-sectional view of the portion of the penis surrounding the tunica 104 during the ablating step 122. As mentioned above, the laser light 117 passes through the openings 160 and ablates portions 170 of the tunica 104 while portions 172 of the tunica that are not exposed to the laser light 117 through the openings 160 are not ablated. In one embodiment, the ablated portions 170 of the tunica 104 are surrounded by non-ablated portions 172.

Figure 5:
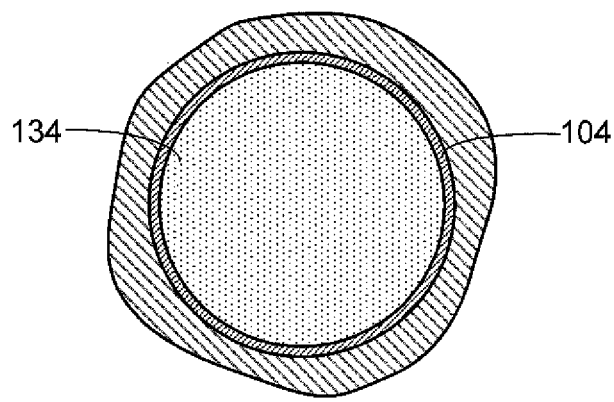
FIG. 5 is a simplified cross-sectional view illustrating the implantation of a penile prosthesis in the tunica.

Following the exposure of the portions of the tunica 104 through the openings 160 of the tube 142 (step 120) and the ablation of portions of the tunica 104 (step 122), the laser fiber 112 is removed (step 130) and the tube 142 is removed from the tunica 104 through the incision 106. As discussed above, a penile prosthesis 134 can then be implanted in the tunica 104 (step 132), as shown in FIG. 5. These steps can be repeated for the other tunica of the patient to complete the penile restoration.

As mentioned above, the tunica ablation treatment performed in accordance with one or more of the embodiments described above may be used to treat Peyronie's disease where scarring of the tunica in various locations causes curvature of the erect penis. In one embodiment, the ablation pattern is formed on the scarred portions of the tunica 104 that require expansion to straighten the curvature of the penis through the performance of embodiments of method steps 110, 120, 122 and 130 discussed above.

In one embodiment, the laser light 117 is pulsed onto the scarred tissue of the tunica in step 120 to form an ablation pattern therein. The ablation pattern allows the scarred tissue to stretch and reduce the curvature of the erect penis caused by the scarred tissue.

In accordance with another embodiment, the pattern of openings 160 on the tube 142 of the device 140 may be customized to match the area of the tunica where the scarring resides. This allows the scarred tissue to be targeted by the laser light 117 while masking other portions of the tunica from the laser light 117. The exposure of the scarred tissue of the tunica 104 through the tube 142 forms the desired ablation pattern on the scarred tissue.

Although the present invention has been described with reference to preferred embodiments, workers skilled in the art will recognize that changes may be made in form and detail without departing from the spirit and scope of the invention.

What is claimed is:

1. A device for use in laser ablation treatments of a tunica of a corpus cavernosum of a patient, the device comprising:
   a cylindrical tube comprising an open proximal end and a plurality of openings through a wall of the tube, the tube configured to dilate the tunica and receive a distal end of a laser fiber; and
   a handle attached to the proximal end;
   wherein:
      the plurality of openings include slits that are non-perpendicular to a central axis of the tube; and
      the wall of the tube is configured to mask portions of the tunica from laser light discharged from within the tube during a laser ablation treatment, whereby an ablation pattern corresponding to the openings is formed on the tunica in response to the laser ablation treatment.

2. The device of claim 1, wherein the handle is displaced from the central axis of the tube.

3. The device of claim 2, further comprising a bent rod having a distal end attached to the proximal end of the tube and a proximal end attached to the handle.

4. The device of claim 3, wherein the handle is substantially parallel to the central axis.

5. The device of claim 1, wherein the tube has a closed distal end.

6. The device of claim 1, wherein the tube has a central axis and the plurality of openings are dispersed in a pattern over the tube.

7. The device of claim 6, wherein a plurality of the slits are parallel to a first plane, which is non-perpendicular to the central axis of the tube.

8. The device of claim 7, wherein a plurality of the slits are parallel to a second plane, which is non-parallel to the first plane and is non-perpendicular to the central axis of the tube.

9. The device of claim 1, wherein the slits are 1.0-15.0 millimeters in length.

10. The device of claim 1, wherein the slits are 0.1-5.0 millimeters in width.

11. The device of claim 1, wherein the device comprises a laser fiber within the cylindrical tube configured to discharge laser light in a radial direction relative to the central axis of the cylindrical tube.

12. The device of claim 1, wherein the openings are angularly displaced around the central axis.

* * * * *

UNITED STATES PATENT AND TRADEMARK OFFICE
CERTIFICATE OF CORRECTION

| | | |
|---|---|---|
| PATENT NO. | : 8,685,011 B2 | Page 1 of 1 |
| APPLICATION NO. | : 13/327012 | |
| DATED | : April 1, 2014 | |
| INVENTOR(S) | : Arcand | |

It is certified that error appears in the above-identified patent and that said Letters Patent is hereby corrected as shown below:

In the Specification

Column 3, Line 20, delete "fiber 114" and insert -- fiber 112 --, therefor.

Signed and Sealed this
Twenty-third Day of December, 2014

Michelle K. Lee
*Deputy Director of the United States Patent and Trademark Office*